US006847746B2

United States Patent
Uchiyama

(10) Patent No.: US 6,847,746 B2
(45) Date of Patent: Jan. 25, 2005

(54) OPTICAL WAVEGUIDE TYPE MICROPLATE

(75) Inventor: Kenichi Uchiyama, Chigasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/367,721

(22) Filed: Feb. 19, 2003

(65) Prior Publication Data

US 2004/0161223 A1 Aug. 19, 2004

(30) Foreign Application Priority Data

Feb. 18, 2002 (JP) .................................. 2002-040418

(51) Int. Cl.[7] .............................................. G02B 6/00

(52) U.S. Cl. .................................. 385/12; 385/147

(58) Field of Search ........................ 385/12, 13, 37, 385/147; 435/6

(56) References Cited

U.S. PATENT DOCUMENTS

| 6,108,463 | A | * | 8/2000 | Herron et al. ................. 385/12 |
| 6,110,749 | A | * | 8/2000 | Obremski et al. ........... 436/527 |
| 2002/0076154 | A1 | * | 6/2002 | Maisenhoelder et al. ..... 385/37 |
| 2003/0132406 | A1 | | 7/2003 | Waldhausl et al. |

* cited by examiner

*Primary Examiner*—John D. Lee
*Assistant Examiner*—Eric Wong
(74) *Attorney, Agent, or Firm*—Pillsbury Winthrop LLP

(57) ABSTRACT

An optical waveguide type microplate includes a substrate, a well formed on one surface of the substrate to receive a solution to be tested, an optical waveguide layer formed on a portion or the whole of a surface of the well contacted with the solution, a light incident member formed on the surface near one end portion in the longitudinal direction of the optical waveguide layer, and a light exist member formed on the surface near other end portion in the longitudinal direction of the optical waveguide layer.

10 Claims, 6 Drawing Sheets

OPTICAL WAVEGUIDE TYPE MICROPLATE

CROSS-REFERENCE TO RELATED APPLICATIONS

This application is based upon and claims the benefit of priority from the prior Japanese Patent Application No. 2002-40418, filed Feb. 18, 2002, the entire contents of which are incorporated herein by reference.

BACKGROUND OF THE INVENTION

1. Field of the Invention

The present invention relates to an optical waveguide type microplate for use in biochemical testing, clinical testing, and the like.

2. Description of the Related Art

For example, an enzyme-linked immuno adsorbent assay method (ELISA method) adopted in clinical testing uses a microplate made of a glass or synthetic resin substrate on the surface of which a plurality of wells are formed. That is, an antibody is immobilized on the well inner surface of this microplate, and a solution to be tested containing an antigen is placed in this well to cause an antigen antibody reaction. Subsequently, an enzyme-labeled antibody is placed in the well and labeled by combining the antibody with the antigen. In addition, a color reagent is placed in the well and allowed to develop color by causing the reagent to react with the enzyme-labeled antibody. The degree of this color development is proportional to the amount of antigen in the solution to be tested. Accordingly, the antigen amount in the solution to be tested can be detected by measuring the coloration degree by an absorbance method by which light is sent in the direction of depth of the solution which has colored.

The reagent used in the ELISA method described above is expensive. To reduce the testing cost, therefore, it is being demanded to reduce the use amount of reagent. However, in the conventional microplate with which light is incident in the direction of depth of a solution to be tested which has colored, the optical path to the colored solution is shortened if the reagent is reduced and the solution to be tested itself is reduced accordingly. This makes accurate absorbance measurement difficult, leading to a decrease in the detection accuracy.

The present invention provides an optical waveguide type microplate capable of accurately measuring absorbance and hence capable of detecting an antigen, antibody, and the like in a solution to be tested, even if the amount of reagent to be added to the solution is reduced.

BRIEF SUMMARY OF THE INVENTION

According to the present invention, there is provided an optical waveguide type microplate comprising:

a substrate;

a well formed on one surface of the substrate to receive a solution to be tested;

an optical waveguide layer formed on a portion or the whole of a surface of the well contacted with the solution;

a light incident member formed on the surface near one end portion in the longitudinal direction of the optical waveguide layer; and a light exist member formed on the surface near other end portion in the longitudinal direction of the optical waveguide layer.

According to the present invention, there is also provided an optical waveguide type microplate comprising:

a substrate;

a plurality of wells formed by mounting, on one surface of a substrate, a frame made of a synthetic resin and integrally having not less than one partition inside, the plurality of wells receiving a solution to be tested;

an optical waveguide layer formed on a portion or the whole of a surface of the well contacted with the solution;

a notch which is formed in the direction of height in the partition where each well is positioned, and through which the needle of an automatic sampler is inserted;

a light incident member formed on the surface near one end portion in the longitudinal direction of the optical waveguide layer; and a light exist member formed on the surface near other end portion in the longitudinal direction of the optical waveguide layer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention and, together with the generation description given above and the detailed description of the preferred embodiments given below, serve to explain the principles of the invention.

DETAILED DESCRIPTION OF THE INVENTION

An optical waveguide type microplate of the present invention will be described in detail below with reference to the accompanying drawing.

Figure 1:
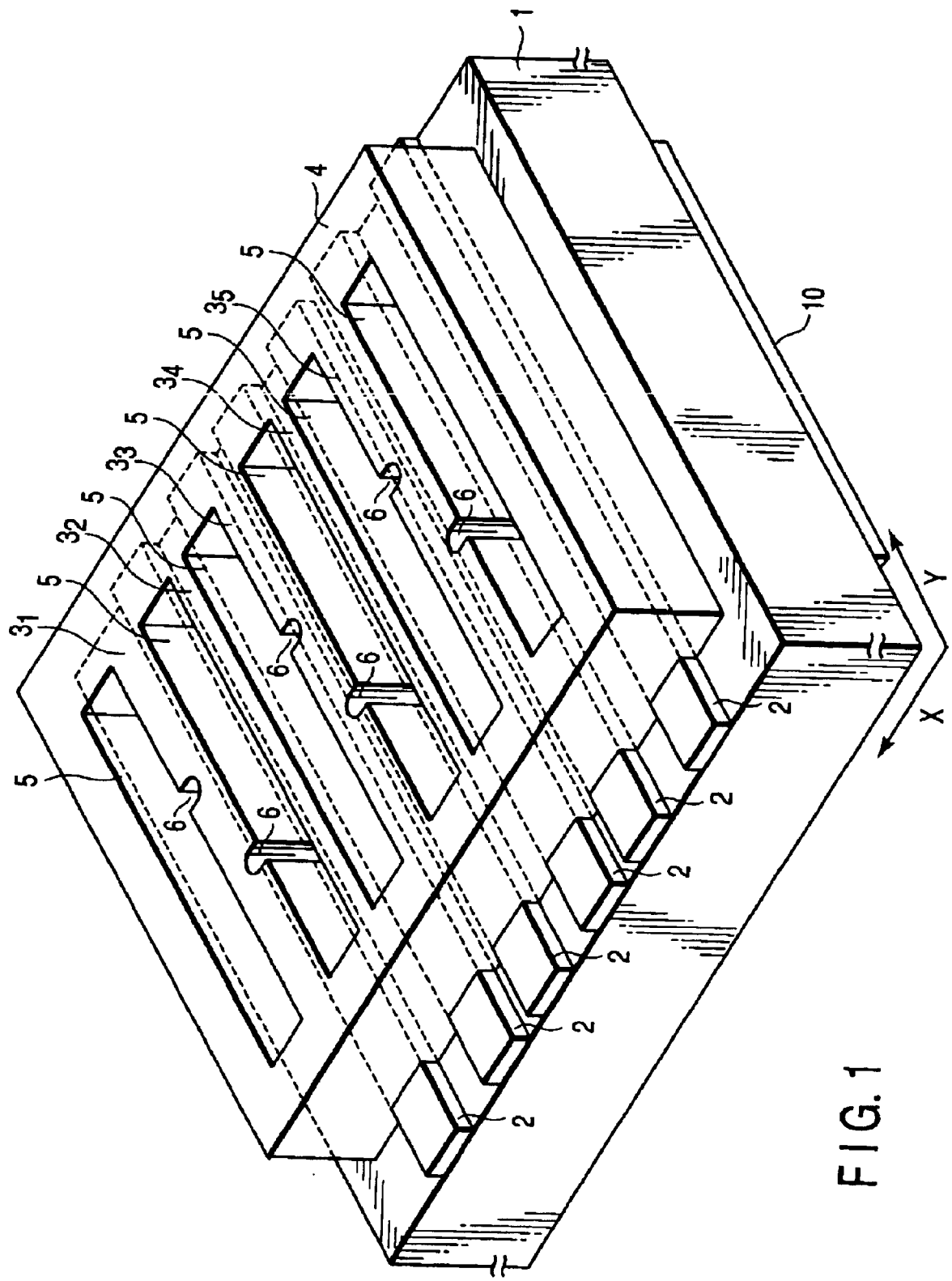
FIG. 1 is a perspective view showing an optical waveguide type microplate used in an embodiment of the present invention.
Figure 2:
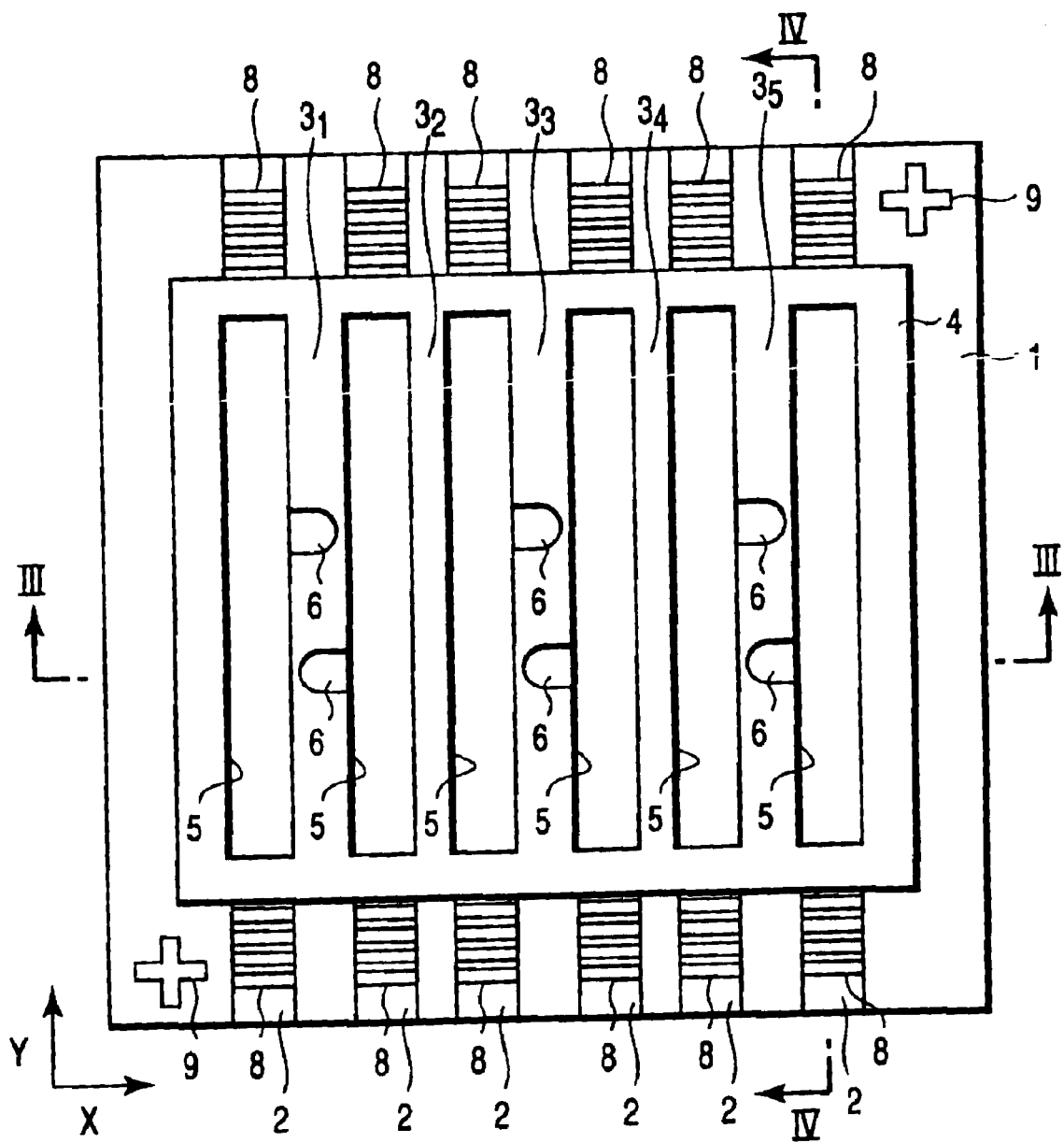
FIG. 2 is a plan view showing the optical waveguide type microplate shown in FIG. 1.
Figure 3:
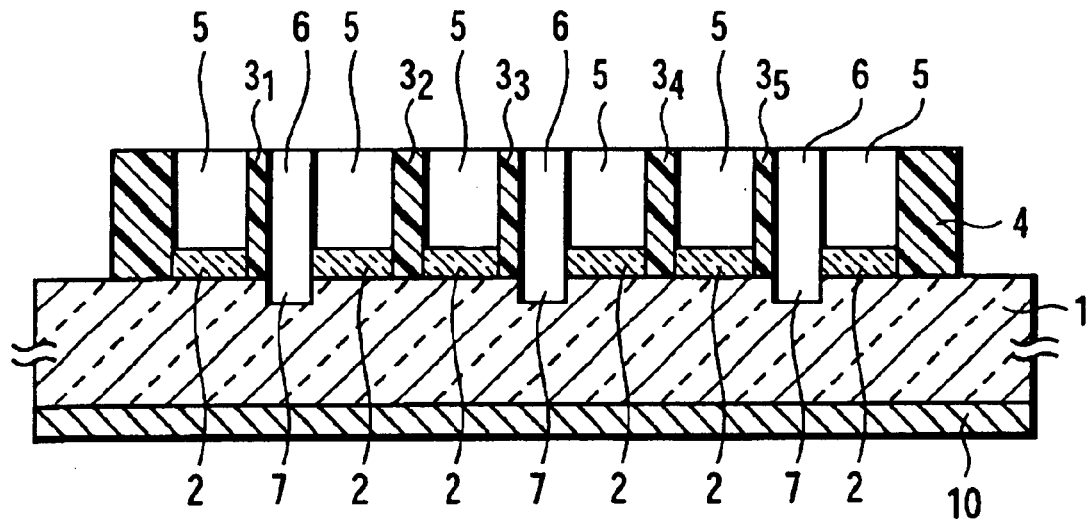
FIG. 3 is a sectional view taken along a line III—III in FIG. 2.
Figure 4:
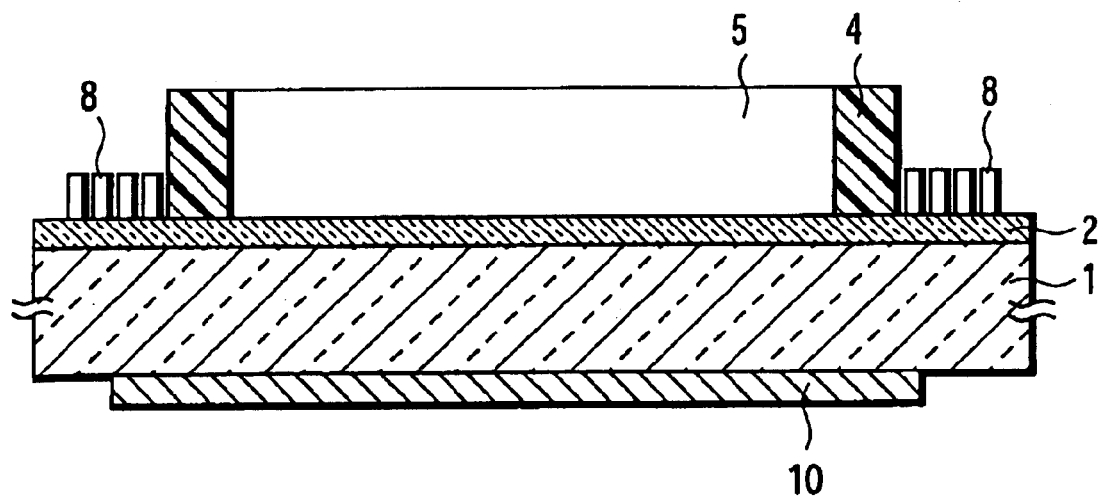
FIG. 4 is a sectional view taken along a line IV—IV in FIG. 2.

FIG. 1 is a perspective view (gratings and alignment marks are not shown) showing an optical waveguide type microplate according to an embodiment of the present invention. FIG. 2 is a plan view of FIG. 1. FIG. 3 is a sectional view taken along a line III—III in FIG. 2. FIG. 4 is a sectional view taken along a line IV—IV in FIG. 2.

As shown in FIGS. 1 and 2, on one surface of a substrate 1 made of glass such as borosilicate glass, six band-like optical waveguide layers 2 extend in the Y-axis direction. These optical waveguide layers 2 have a refractive index higher than that of the substrate 1. Each optical waveguide layer 2 is formed by ion exchange of an element such as potassium or sodium with the glass component of the glass substrate 1.

The material of the substrate 1 is not limited to borosilicate glass. That is, it is also possible to use silica glass or a synthetic resin such as a polyacrylic resin, polycarbonate resin, norbornene resin, or polyethyleneterephthalate resin.

A frame 4 integrally having a plurality of, e.g., five parallel partitions $3_1$ to $3_5$ inside is mounted on the substrate 1 via an adhesive layer (not shown) or the like. Six band-like spaces are formed between the frame 4 and partitions $3_1$ and $3_5$ and between the partitions $3_2$ to $3_4$. These band-like spaces match the band-like optical waveguide layers 2. Those walls of the frame 4, which extend in the X-axis direction are formed across the optical waveguide layers 2. By thus mounting the frame 4 integrally having the five partitions $3_1$ to $3_5$ on the substrate 1, wells 5 are formed in portions corresponding to the six band-like spaces. Also, the optical waveguide layers 2 are positioned on the entire bottom portions of these wells 5. The partitions $3_1$ to $3_5$ and frame 4 are made of a synthetic resin such as a polyacrylic resin or polycarbonate resin.

Six notches 6 into which the needles of an automatic sampler are inserted are formed in the direction of height in the side walls of the partitions $3_1$, $3_3$, and $3_5$ adjacent to the wells 5. Two notches 6 formed in the two side walls of each of the partitions $3_1$, $3_3$, and $3_5$ are misaligned from each other in the Y-axis direction. As shown in FIG. 3, recesses (escape portions) 7 are formed in those portions of the surface layer of the substrate 1, which are immediately below the notches 6.

Two gratings 8 are formed on the surface near those two end portions in the longitudinal direction of each optical waveguide layer 2, which are positioned outside the frame 4. These gratings 8 function as a light incident member and light exit member. The gratings 8 have a refractive index higher than that of the optical waveguide layers 2. Each grating 8 is made of, e.g., a photoresist. Alignment marks 9 are formed on the opposite corners of the substrate 1. A high-thermal-conductivity film 10 is formed on the lower surface of the substrate 1 except for a light incident region and light exit region. As this high-thermal-conductivity film 10, a metal film such as a copper or aluminum film or a ceramic film such as an aluminum nitride or boron nitride film is used.

An example of a method of manufacturing the aforementioned optical waveguide type microplate will be explained below with reference to FIGS. 5A to 5D.

Figure 5A:
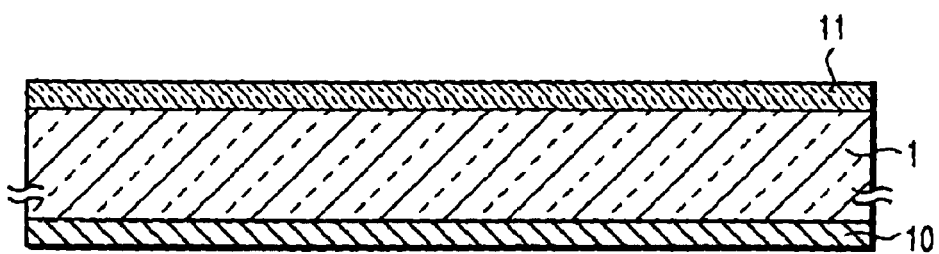
FIGS. 5A to 5D are sectional views showing the steps of manufacturing the optical waveguide type microplate shown in FIG. 1.
Figure 5B:
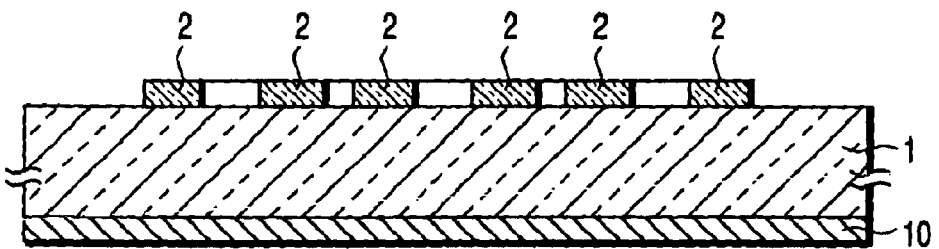

First, as shown in FIG. 5A, a high-thermal-conductivity film 10 is formed on the lower surface of a substrate 1 made of borosilicate glass or the like, except for a light incident region and light exit region. The surface of this substrate 1 is then dipped in an ion-exchanging solution such as a potassium nitrate molten salt at, e.g., 380 to 400° C., thereby forming an ion exchange layer 11 by ion exchange of potassium as a high-refractive-index element with the component of borosilicate glass. Subsequently, this ion exchange layer 11 is patterned to form, e.g., six band-like optical waveguide layers 2 as shown in FIG. 5B.

Figure 5C:
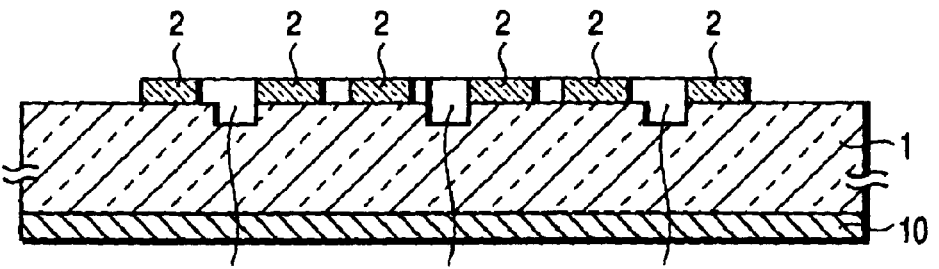

As shown in FIG. 5C, recesses (escape portions) are formed in the surface layer of the substrate 1. The entire surface is then coated with a photoresist film. After this photoresist film is dried, exposure and development are performed to form gratings (not shown) on the surface near the two end portions in the longitudinal direction of each optical waveguide layer 2. After that, alignment marks (not shown) are formed on the opposite corners of the substrate 1.

Figure 5D:
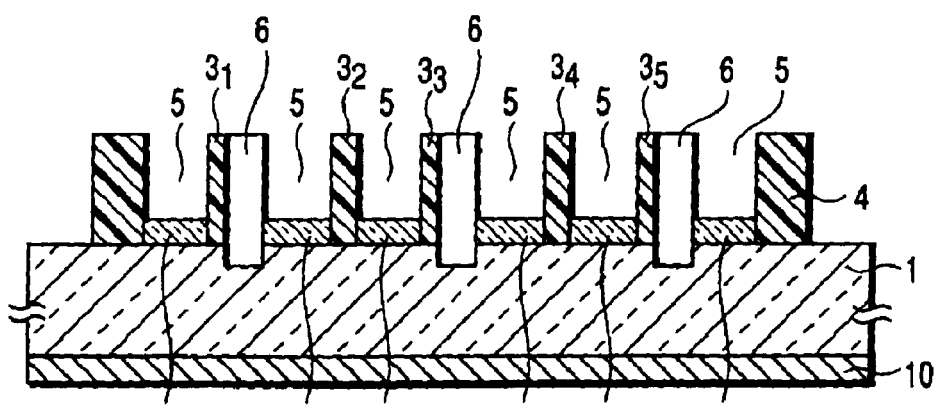

Subsequently, a frame 4 integrally having a plurality of, e.g., five parallel partitions $3_1$ to $3_5$ inside is mounted on the substrate 1 via an adhesive layer (not shown) or the like. As a consequence, six band-like spaces are formed between the frame 4 and partitions $3_1$ and $3_5$ and between the partitions $3_2$ to $3_4$. These band-like spaces match the band-like optical waveguide layers 2. Those walls of the frame 4, which extend in the X-axis direction are formed across the optical waveguide layers 2. By thus forming the frame 4 integrally having the five partitions $3_1$ to $3_5$ on the substrate 1, wells 5 are formed in portions corresponding to the six band-like spaces. At the same time, six notches 6 formed in the direction of height in the side walls of the partitions $3_1$, $3_3$, and $3_5$ are matched with the recesses 7. These notches 6 are misaligned from each other in the Y-axis direction in the two side walls of each of the partitions $3_1$, $3_3$, and $3_5$. Through these steps, an optical waveguide type microplate shown in FIG. 5D is manufactured. The function of the optical waveguide type microplate according to the present invention will be described below with reference to FIGS. 1 to 4 explained above and FIGS. 6 and 7.

Figure 6:
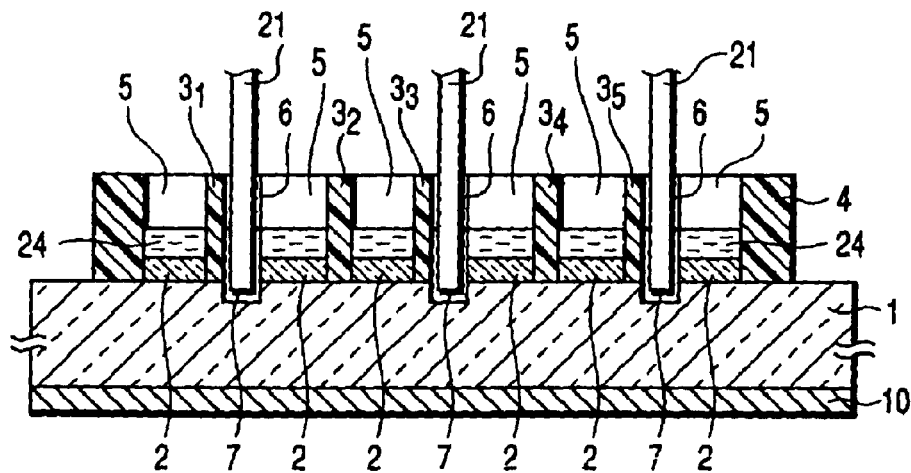
FIG. 6 is a sectional view for explaining the function of the optical waveguide type microplate of the present invention.
Figure 7:
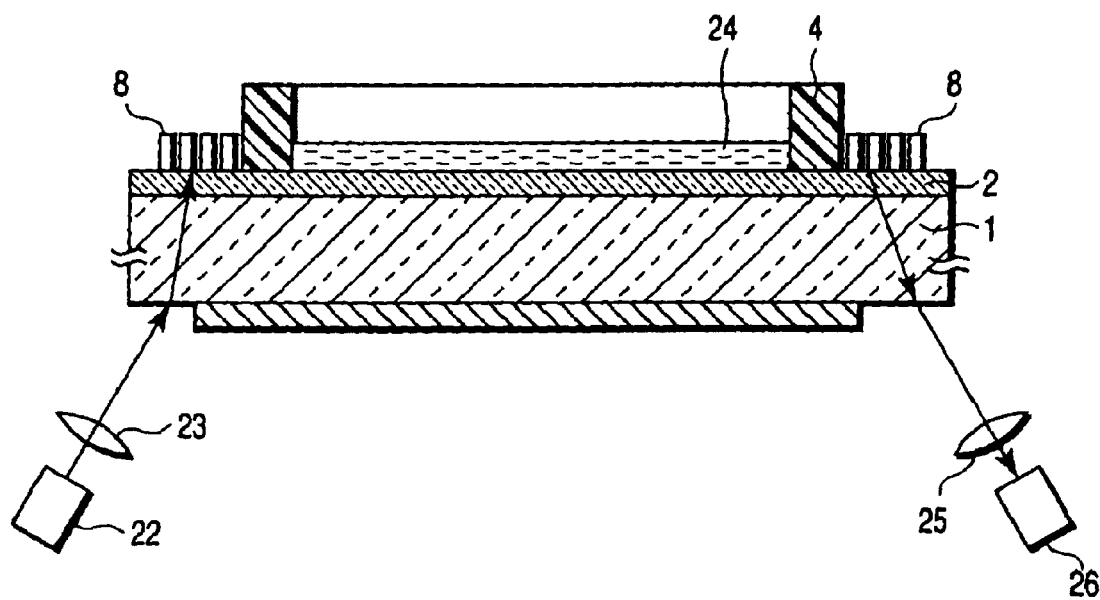
FIG. 7 is a sectional view for explaining the function of the optical waveguide type microplate of the present invention.

As shown in FIG. 6, needles 21 of an automatic sampler are positioned immediately above the notches 6 formed in the side walls of the partitions $3_1$, $3_3$, and $3_5$ of the frame 4 with reference to the alignment marks 9 on the substrate 1. These needles 21 are then inserted into these notches 6 and into the recesses 7 immediately below the notches 6. For example, an antibody is supplied into the six wells 5 through these automatic sampler's needles 21 and immobilized on those inner surfaces of these wells 5, which include the optical waveguide layers 2 on the bottom surfaces of the wells 5.

The automatic sampler needles 21 are removed. The needles (not shown) of another automatic sampler are then inserted into the notches 6 formed in the side walls of the partitions $3_1$, $3_3$, and $3_5$ of the frame 4 and into the recesses 7 immediately below these notches 6. A solution to be tested, e.g., blood is supplied into the wells 5 through these automatic sampler's needles, thereby causing an antigen in the blood to react with the antibody immobilized on the surfaces of the optical waveguide layers 2 in these wells 5. Furthermore, an enzyme-labeled antibody is supplied into the wells 5 through the needles of still another automatic sampler and labeled by combining the antibody with the antigen. Subsequently, a color reagent is supplied into the wells 5 through the needles of still another automatic sampler and allowed to develop color by causing the reagent to react with the enzyme-labeled antibody. In these reactions, the solution to be tested and reagent in each well 5 can be set at uniform temperatures because the high-thermal-conductivity film is formed on the lower surface of the substrate 1.

After the color development reaction as described above, as shown in FIG. 7, laser beams are sent from, e.g., six laser light sources 22 to become incident on the lower surface of the substrate 1 of the microplate through polarizing filters 23. Each laser beam passes through the substrate 1 and is refracted by the interface between the grating 8 and the optical waveguide layer 2 on the bottom surface of each well 5 containing a colored solution 24. The refracted laser beam enters and propagates in the optical waveguide layer 2. During the course of this propagation, an evanescent wave is emitted to the colored solution 24 in each well 5 and absorbed by a dye. The light propagating in the optical waveguide layer 2 in each well 5 is emitted from the grating 8 on the opposite side. The emitted light is received by a light-receiving element 26 through a polarizing filter 25, and the transmitted light intensity is measured. Consequently, the antigen amount in the blood in each well 5 is detected.

After the antigen amount in the blood is thus detected, the colored solution in each well 5 is discharged through the automatic sampler's needle, the well 5 is cleaned, and, for example, the antigen amount in the blood is measured again.

In the present invention as described above, blood as a solution to be tested is subjected to an antigen antibody reaction, an enzyme-labeled antibody is combined with the antigen, and a color reagent is allowed to develop color by a reaction with the enzyme-labeled antibody in each well 5. After that, light is fed into the optical waveguide layer 2 on the bottom surface of each well 5, i.e., light is incident in the direction of surface of each well 5, and the transmitted light intensity of the light emitted after propagating in the optical waveguide layer 2 is measured. In this way, the antigen amount in the blood can be detected in each well 5. Accordingly, the antigen amount in the blood can be detected by supplying, into each well 5, only a small amount of blood or reagent with which the surface of the optical waveguide layer 2 is covered. As a consequence, compared to the conventional method in which light is transmitted in the direction of depth of a colored solution in a well, the use amounts of solution to be tested and reagent can be reduced, and the detection cost can be reduced.

Also, the recess 7 is formed in that portion of the substrate 1, which is immediately below the notch 6 into which the needle of an automatic sampler is inserted, so the lower end of the automatic sampler's needle can be inserted to this recess 7. Therefore, the tested solution in the well 5 does not remain on the surface of the optical waveguide layer 2 on the bottom surface of the well 5, but can be easily discharged through the automatic sampler's needle. This allows the next detecting operation to be performed without any decrease in the detection accuracy caused by the residual solution.

Furthermore, the high-thermal-conductivity film 10 is attached to the lower surface of the substrate 1. This makes the temperatures of the solution to be tested and reagent in each well 5 uniform, and thereby makes highly accurate detection feasible.

The optical waveguide type microplate according to the present invention is not limited to the structure shown in FIGS. 1 to 4 described previously, and can also have the following structures.

Figure 8:
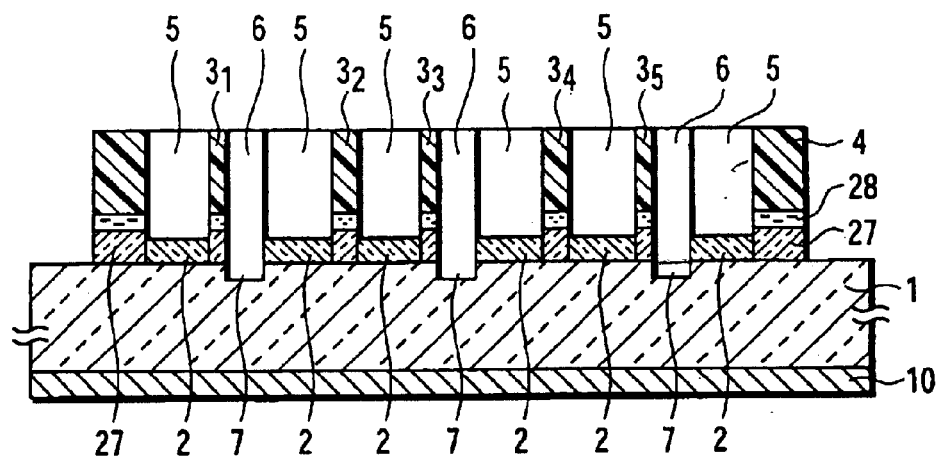
FIG. 8 is a sectional view showing another embodiment of the optical waveguide type microplate of the present invention.

(1) As shown in FIG. 8, a frame 4 integrally having five partitions $3_1$ to $3_5$ is mounted on the substrate 1 via an adhesive layer 28 in the same manner as in the above embodiment. A frame-like layer 27 is formed on the surface of the substrate 1 as an undercoating of the adhesive layer 28. This frame-like layer 27 is made of a material, e.g., fluorine-added silicon (SiOF), having a refractive index higher than that of the optical waveguide layer 2.

With this arrangement, the adhesive layer 28 having a refractive index lower than that of the optical waveguide layer 2 is not in direct contact with the optical waveguide layer 2. Hence, light can propagate in the optical waveguide layer 2 without leaking from a portion in contact with the adhesive layer 28.

Figure 9:
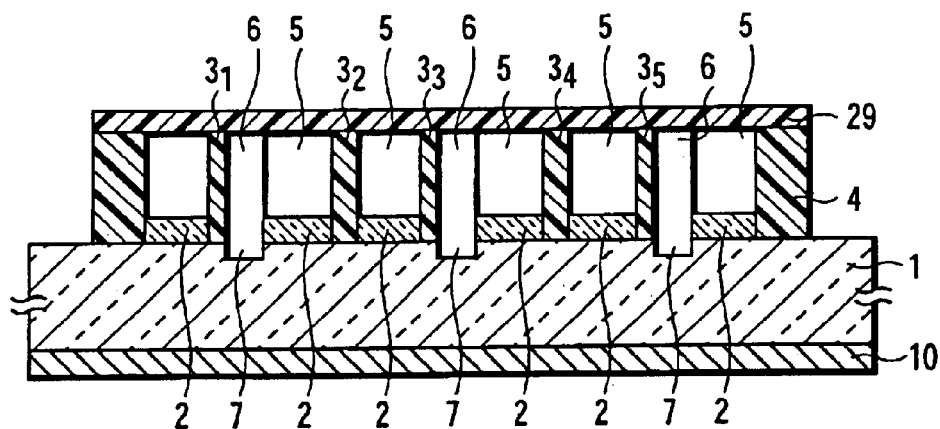
FIG. 9 is a sectional view showing still another embodiment of the optical waveguide type microplate of the present invention.

(2) As shown in FIG. 9, a cover 29 made of a film is attached, by thermocompression or the like, to the upper surface of a frame 4 integrally having five partitions $3_1$ to $3_5$. This film is made of a material through which the needle of an automatic sampler can easily penetrate when inserted.

With this arrangement, the cover 29 can prevent evaporation of a solution in each well 5. Also, the needle of an automatic sampler can be inserted through this cover 29.

Figure 10:
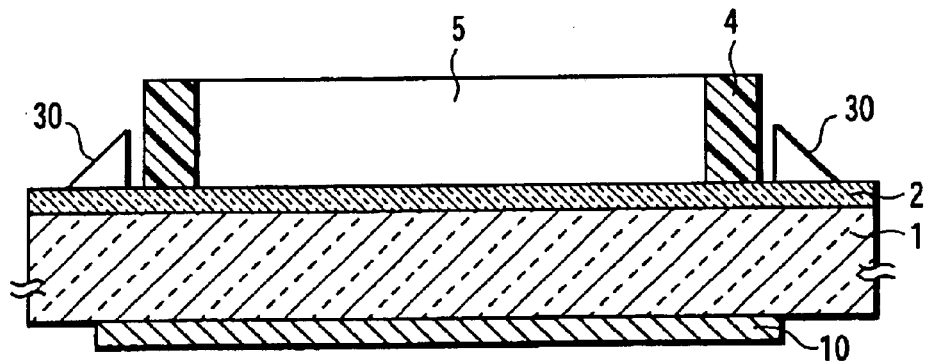
FIG. 10 is a sectional view showing still another embodiment of the optical waveguide type microplate of the present invention.

(3) As shown in FIG. 10, prisms 30, instead of gratings, can be attached to the surface near those two end portions of each optical waveguide layer 2, which are positioned outside the frame 4.

(4) Although not shown, a cladding layer can be formed on a substrate as an undercoating of an optical waveguide layer.

In the embodiments of the present invention, the number of wells formed on a substrate is not restricted to six. That is, one or a plurality of wells other than six can also be formed on a substrate.

In the embodiments of the present invention, light is fed into an optical waveguide layer and allowed to propagate, and the transmitted light intensity of the emitted light is measured. However, it is also possible to allow the evanescent wave which is generated when the light propagates in the optical waveguide layer to cause a colored solution to excite fluorescence, and measure this fluorescence by a light-receiving element placed above the well, thereby detecting the antigen amount in the blood in the well.

In the embodiments of the present invention, blood is used as a solution to be tested. However, it is also possible to use, e.g., a humor of an animal as an object of biochemical testing or clinical testing.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An optical waveguide type microplate comprising:
   a substrate;
   a frame integrally having at least one partition inside said frame and disposed on the substrate, said frame and said at least one partition defining a plurality of wells, the plurality of wells receiving a solution to be tested;
   an optical waveguide layer formed on at least a portion of a surface of the well in contact with the solution;
   a light incident member formed on a surface near another end portion in a longitudinal direction of the optical waveguide layer; and
   a light exit member formed on a surface near another end portion in the longitudinal direction of the optical waveguide layer, wherein the partition defines a notch which is formed in a direction of height in the partition where each well is positioned, and through which a needle of an automatic sampler is inserted, and a recess is formed in a portion of a surface layer of the substrate, which is immediately below the notch.

2. A microplate according to claim 1, wherein the substrate is made of glass.

3. A microplate according to claim 1, wherein the optical waveguide layer is made of a material having a refractive index higher than a refractive index of the substrate.

4. A microplate according to claim 1, wherein the frame and the at least one partition are made of a synthetic resin.

5. A microplate according to claim 1, further comprising a synthetic resin cover attached to an upper surface of the frame.

6. A microplate according to claim 1, wherein the light incident member and light exit member include gratings.

7. A microplate according to claim 1, wherein the light incident member and light exit member include prisms.

8. A microplate according to claim 1, further comprising an alignment mark formed on a surface region of the substrate except for the well.

9. A microplate according to claim 1, further comprising a high-thermal-conductivity film formed on a desired portion of the lower surface of the substrate.

10. A microplate according to claim 9, wherein the high-thermal-conductivity film is one member selected from the group consisting of a metal film, aluminum nitride film, and boron nitride film.

* * * * *